(12) United States Patent
Shevgoor

(10) Patent No.: US 9,402,975 B2
(45) Date of Patent: Aug. 2, 2016

(54) SYSTEMS AND METHODS TO INCREASE RIGIDITY AND SNAG-RESISTANCE OF CATHETER TIP

(75) Inventor: Siddarth K. Shevgoor, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 246 days.

(21) Appl. No.: 13/223,178

(22) Filed: Aug. 31, 2011

(65) Prior Publication Data
US 2013/0053826 A1    Feb. 28, 2013

(51) Int. Cl.
*A61M 25/00*    (2006.01)

(52) U.S. Cl.
CPC ......... *A61M 25/007* (2013.01); *A61M 25/0015* (2013.01); *A61M 25/008* (2013.01); *A61M 25/0068* (2013.01); *A61M 2025/0073* (2013.01); *Y10T 29/49826* (2015.01)

(58) Field of Classification Search
CPC .......... A61M 25/0071; A61M 25/007; A61M 25/0067; A61M 1/0092; A61M 1/008; A61M 25/0015
USPC ........................... 604/509, 524, 529, 585, 523
See application file for complete search history.

(56) References Cited

U.S. PATENT DOCUMENTS

| | | | | |
|---|---|---|---|---|
| 1,879,249 A | * | 9/1932 | Honsaker | A61M 25/0021 604/27 |
| 3,713,442 A | | 1/1973 | Walter | |
| 4,563,180 A | | 1/1986 | Jervis et al. | |
| 4,583,968 A | * | 4/1986 | Mahurkar | A61M 5/1582 604/43 |
| 4,639,252 A | * | 1/1987 | Kelly | A61M 25/0021 604/541 |
| 4,661,094 A | * | 4/1987 | Simpson | A61B 17/22 604/8 |
| 4,717,379 A | * | 1/1988 | Ekholmer | A61M 25/007 604/43 |
| 4,717,381 A | | 1/1988 | Papantonakos | |
| 4,784,638 A | | 11/1988 | Ghajar et al. | |
| 4,894,057 A | * | 1/1990 | Howes | A61B 5/02152 604/43 |
| 4,895,561 A | * | 1/1990 | Mahurkar | A61M 5/1582 604/174 |
| 4,950,232 A | * | 8/1990 | Ruzicka | A61M 1/008 604/103.01 |
| 4,961,731 A | | 10/1990 | Bodicky et al. | |
| 4,968,307 A | | 11/1990 | Dake et al. | |
| 5,037,403 A | | 8/1991 | Garcia | |
| 5,085,635 A | * | 2/1992 | Cragg | A61M 25/0075 604/102.03 |
| 5,088,991 A | | 2/1992 | Weldon | |

(Continued)

FOREIGN PATENT DOCUMENTS

| | | |
|---|---|---|
| DE | 10 2006 052 612 B3 | 2/2008 |
| EP | 0 299 622 A2 | 6/1988 |

(Continued)

OTHER PUBLICATIONS

Weber, Paul W. et al., "AJR: Modified Catheter Can Reduce Contrast Material Injuries," Health Imaging.com, Clinical Studies, http://www.healthimaging.com/index.php?view=article&id=18807%3Aajr-modified-cath . . . , 1 page, Oct. 21, 2009.

*Primary Examiner* — Kami A Bosworth
*Assistant Examiner* — Matthew A Engel
(74) *Attorney, Agent, or Firm* — Jeanne Lukasavage; Craig Metcalf; Kirton McConkie

(57) ABSTRACT

A venous catheter having a catheter tip comprising recessed diffusion holes for increasing the snag-resistance of the venous catheter. The invention further provides systems and methods for providing axial ridges interposed between diffusion holes for increasing the rigidity of the vented catheter tip.

20 Claims, 9 Drawing Sheets

(56) References Cited

U.S. PATENT DOCUMENTS

| | | | |
|---|---|---|---|
| 5,135,599 A * | 8/1992 | Martin | A61M 25/0009 156/294 |
| 5,180,364 A * | 1/1993 | Ginsburg | A61M 25/0075 600/435 |
| 5,201,723 A | 4/1993 | Quinn | |
| 5,221,256 A * | 6/1993 | Mahurkar | A61M 25/0026 604/43 |
| 5,234,406 A | 8/1993 | Drasner et al. | |
| 5,250,034 A | 10/1993 | Appling et al. | |
| 5,267,979 A | 12/1993 | Appling et al. | |
| 5,334,154 A | 8/1994 | Samson et al. | |
| 5,364,344 A * | 11/1994 | Beattie | A61M 25/003 604/43 |
| 5,374,245 A * | 12/1994 | Mahurkar | A61M 25/001 604/43 |
| 5,380,307 A * | 1/1995 | Chee | A61M 25/0054 604/264 |
| 5,451,216 A * | 9/1995 | Quinn | A61M 1/008 604/270 |
| 5,507,995 A * | 4/1996 | Schweich, Jr. | A61M 25/0013 264/293 |
| 5,536,261 A | 7/1996 | Stevens | |
| 5,542,925 A | 8/1996 | Orth | |
| 5,571,093 A * | 11/1996 | Cruz | A61M 25/0026 604/264 |
| 5,578,006 A | 11/1996 | Schön | |
| 5,616,137 A | 4/1997 | Lindsay | |
| 5,643,228 A * | 7/1997 | Schucart | A61M 25/007 604/264 |
| 5,647,846 A | 7/1997 | Berg et al. | |
| 5,830,181 A | 11/1998 | Thornton | |
| 5,843,017 A | 12/1998 | Yoon | |
| 5,857,464 A | 1/1999 | Desai | |
| 6,052,612 A | 4/2000 | Desai | |
| 6,129,700 A | 10/2000 | Fitz | |
| 6,132,405 A | 10/2000 | Nilsson et al. | |
| 6,221,049 B1 * | 4/2001 | Selmon | A61B 17/3207 600/585 |
| 6,293,958 B1 | 9/2001 | Berry et al. | |
| 6,514,236 B1 | 2/2003 | Stratienko | |
| 6,533,763 B1 * | 3/2003 | Schneiter | A61M 25/007 604/264 |
| 6,540,714 B1 * | 4/2003 | Quinn | A61M 25/0069 138/177 |
| 6,547,769 B2 | 4/2003 | VanTassel et al. | |
| 6,641,564 B1 | 11/2003 | Kraus | |
| 6,659,134 B2 * | 12/2003 | Navis | A61M 1/285 138/116 |
| 6,669,679 B1 | 12/2003 | Savage et al. | |
| 6,702,776 B2 * | 3/2004 | Quinn | A61M 25/0069 138/177 |
| 6,758,836 B2 * | 7/2004 | Zawacki | A61M 1/3653 604/284 |
| 6,758,857 B2 * | 7/2004 | Cioanta | A61B 18/04 604/101.01 |
| 6,858,019 B2 * | 2/2005 | McGuckin, Jr. | A61M 1/285 604/43 |
| 6,866,655 B2 | 3/2005 | Hackett | |
| 7,108,674 B2 | 9/2006 | Quinn | |
| 8,066,660 B2 * | 11/2011 | Gregersen | A61M 1/3653 604/29 |
| 8,152,951 B2 * | 4/2012 | Zawacki | A61M 1/3653 156/290 |
| 8,292,841 B2 * | 10/2012 | Gregersen | A61M 1/3653 604/29 |
| 8,323,227 B2 * | 12/2012 | Hamatake | A61M 1/3653 604/264 |
| 8,747,343 B2 * | 6/2014 | MacMeans | A61M 1/3653 604/264 |
| 8,876,752 B2 * | 11/2014 | Hayakawa | A61M 1/3653 604/29 |
| 9,044,576 B2 * | 6/2015 | Onuma | A61M 25/0075 |
| 2002/0072712 A1 | 6/2002 | Nool et al. | |
| 2003/0023200 A1 | 1/2003 | Barbut et al. | |
| 2003/0093027 A1 * | 5/2003 | McGuckin, Jr. | A61M 1/285 604/6.16 |
| 2004/0159360 A1 * | 8/2004 | Navis | A61M 1/285 138/116 |
| 2004/0193102 A1 * | 9/2004 | Haggstrom | A61M 1/3661 604/43 |
| 2005/0124969 A1 | 6/2005 | Fitzgerald et al. | |
| 2005/0192560 A1 | 9/2005 | Walls et al. | |
| 2005/0197633 A1 | 9/2005 | Schwartz et al. | |
| 2006/0004316 A1 * | 1/2006 | Difiore | A61M 25/0068 604/6.16 |
| 2006/0184048 A1 | 8/2006 | Saadat | |
| 2007/0073271 A1 | 3/2007 | Brucker et al. | |
| 2007/0191810 A1 * | 8/2007 | Kennedy | A61M 25/00 604/508 |
| 2009/0118661 A1 * | 5/2009 | Moehle | A61M 25/0068 604/6.16 |
| 2009/0287186 A1 * | 11/2009 | Adams | A61M 25/0009 604/523 |
| 2010/0286657 A1 | 11/2010 | Heck | |
| 2011/0130745 A1 * | 6/2011 | Shevgoor | A61M 5/14 604/523 |
| 2012/0022502 A1 | 1/2012 | Adams et al. | |
| 2012/0245562 A1 * | 9/2012 | Bihlmaier | A61M 25/0074 604/523 |

FOREIGN PATENT DOCUMENTS

| | | |
|---|---|---|
| EP | 0 947 211 A2 | 10/1999 |
| FR | 2788223 A1 | 7/2000 |
| WO | 01/93935 A1 | 12/2001 |
| WO | WO 01/91830 A1 | 12/2001 |

* cited by examiner

SYSTEMS AND METHODS TO INCREASE RIGIDITY AND SNAG-RESISTANCE OF CATHETER TIP

BACKGROUND OF THE INVENTION

The present invention relates generally to vascular infusion systems and components, including catheter assemblies and devices used with catheter assemblies. In particular, the present invention relates to systems and methods for increasing the rigidity and snag-resistance of a catheter tip of a vascular infusion system having catheter hole arrays to provide enhanced infusion flow rates, lower system pressures, and reduced catheter exit jet velocities. Additionally, the present invention relates to improving the overall rigidity of a thin-walled structure.

Vascular access devices are used for communicating fluid with the anatomy of a patient. For example, vascular access devices, such as catheters, are commonly used for infusing fluid, such as saline solution, various medicaments, and/or total parenteral nutrition, into a patient, withdrawing blood from a patient, and/or monitoring various parameters of the patient's vascular system.

A variety of clinical circumstances, including massive trauma, major surgical procedures, massive burns, and certain disease states, such as pancreatitis and diabetic ketoacidosis, can produce profound circulatory volume depletion. This depletion can be caused either from actual blood loss or from internal fluid imbalance. In these clinical settings, it is frequently necessary to infuse blood and/or other fluid rapidly into a patient to avert serious consequences.

Additionally, the ability to inject large quantities of fluid in a rapid manner may be desirable for certain other medical and diagnostic procedures. For example, some diagnostic imaging procedures utilize contrast media enhancement to improve lesion conspicuity in an effort to increase early diagnostic yield. These procedures necessitate viscous contrast media be injected by a specialized "power injector" pump intravenously at very high flow rates, which establishes a contrast bolus or small plug of contrast media in the bloodstream of the patient which results in enhanced image quality.

Power injection procedures generate high pressures within the infusion system, thereby requiring specialized vascular access devices, extension sets, media transfer sets, pump syringes, and bulk or pre-filled contrast media syringes. As the concentration (and thereby viscosity) and infusion rate of the contrast media are increased, bolus density also increases resulting in better image quality via computed tomography (CT) attenuation. Therefore, a current trend in healthcare is to increase the bolus density of the contrast media by increasing both the concentration of the contrast media and the rate at which the media is infused into the patient, all of which ultimately drives system pressure requirements higher.

Intravenous infusion rates may be defined as either routine, generally up to 999 cubic centimeters per hour (cc/hr), or rapid, generally between about 999 cc/hr and 90,000 cc/hr (1.5 liters per minute) or higher. For some diagnostic procedures utilizing viscous contrast media, an injection rate of about 1 to 10 ml/second is needed to ensure sufficient bolus concentration. Power injections of viscous media at this injection rate produce significant back pressure within the infusion system that commonly results in a failure of the infusion system components.

Traditionally, rapid infusion therapy entails the use of an intravenous catheter attached to a peristaltic pump and a fluid source. A patient is infused as a tip portion of the catheter is inserted into the vasculature of a patient and the pump forces a fluid through the catheter and into the patient's vein. Current rapid infusion therapies utilize a catheter and catheter tip with geometries identical to those used with traditional, routine infusion rates. These geometries include a tapering catheter tip such that the fluid is accelerated as the fluid moves through the catheter tip and exits into a patient's vasculature. This acceleration of the infused fluid is undesirable for several reasons.

For example, the tapered catheter results in a greater backpressure for the remainder of the catheter assembly. This effect is undesirable due to the limitations of the pumping capacity of the infusion pump as well as the limited structural integrity of the components and subcomponents of the infusion system. For example, if the backpressure becomes too great, the pump's efficiency may decrease and certain seals or connections within the infusion system may fail. Additionally, the fluid acceleration in the catheter tip results in a recoil force that may cause the catheter tip to shift within the patient's vein thereby displacing the catheter and/or damaging the patient's vein and/or injection site. Fluid acceleration also increases the jet velocity of the infusant at the tip of the catheter. In some procedures, the fluid jet may pierce the patient's vein wall thereby leading to extravasation or infiltration. Not only is this uncomfortable and painful to the patient, but infiltration may also prevent the patient from receiving the needed therapy.

To overcome undesirable backpressures and increased acceleration of infused fluids, some intravascular systems include arrays of diffuser holes provided in and around the tip portion of the intravenous catheter. Examples of arrays of diffuser holes and diffuser hole geometries are provided in U.S. patent application Ser. Nos. 12/427,633 and 13/022,501, each of which are incorporated herein by reference.

In general, diffuser holes increase the surface area of the catheter tip opening thereby decreasing fluid pressure at the catheter tip opening. However, addition of diffuser holes at or near the tip of a catheter also reduces the buckling resistance of the catheter thereby making the catheter tip more susceptible to crushing during insertion. As a result, the addition of diffuser holes may result in failed catheterization and physical pain to the patient. Further, addition of diffuser holes provides the catheter with a non-continuous outer surface that may snag or catch on the opening of the patient's skin and/or vein through which the catheter is inserted. This too may result in failed catheterization, physical pain and/or physical damage to the patient.

Thus, while methods and systems currently exist to reduce exit velocity of an infusant during rapid infusion procedures, challenges still exist. Accordingly, it would be an improvement in the art to augment or even replace current techniques with other techniques.

BRIEF SUMMARY OF THE INVENTION

The systems and methods of the present disclosure have been developed in response to problems and needs in the art that have not yet been fully resolved by currently available infusion systems and methods. Thus, these systems and methods are developed to provide for safer and more efficient rapid infusion procedures.

One aspect of the present invention provides an improved vascular access device for use in combination with a vascular infusion system capable of rapidly delivering an infusant to the vascular system of a patient. The vascular access device generally includes an intravenous catheter configured to access the vascular system of a patient. The intravenous catheter is coupled to the vascular infusion system via a section of intravenous tubing. The material of the intravenous catheter may include a polymer or metallic material compatible with infusion procedures.

In some embodiments, a tip portion of the intravenous catheter is modified to include a plurality of diffusion holes. The tip portion generally comprises a tapered profile, wherein the outer and inner surface of the tip taper towards the distal end of the catheter. The tapered outer surface provides a smooth transition between the narrow diameter of the catheter tip opening and the larger diameter of the catheter tubing. Thus, as the tip of the catheter is introduced into the vein of a patient, the tapered outer surface facilitates easy insertion of the catheter through the access hole. The tapered inner surface is generally provided to tightly contact the outer surface of an introducer needle housed within the lumen of the catheter. The introducer needle is provided to create an opening into the vein of patient through which the catheter tip is inserted. The tapered inner surface ensures a tight seal between the inner surface of the catheter and the outer surface of the needle. Following placement of the catheter, the introducer needle is removed.

In some implementations, a peripheral catheter is provided comprising a catheter body having an outer surface, a proximal end, a distal end, a lumen extending between the proximal and distal ends, and a distal lumen opening, the catheter further including a recess formed in the outer surface of the catheter body. In some implementations, a diffusion hole is further positioned within the recess through a wall thickness of the catheter body. As such, the recessed location of the diffusion hole is removed from directly contacting the skin or other tissues of the patient during insertion of the catheter. Accordingly, the diffusion hole is prevented from snagging the skin or tissues of the patient.

In some implementations, a method for manufacturing a snag-resistant, vented catheter is provided, wherein the method includes the steps of providing a catheter body having an outer surface, a proximal end, a distal end, a lumen extending between the proximal and distal ends, and a lumen opening. The method further includes the steps of providing a recess in the outer surface of the catheter body, and further providing a diffusion hole in the recess through a wall thickness of the catheter body. As such, the recessed location of the diffusion hole is removed from directly contacting the skin or other tissues of the patient during insertion of the catheter. Accordingly, the diffusion hole is prevented from snagging the skin or tissues of the patient.

Further, in some implementations, a peripheral catheter is provided comprising a catheter body having a predetermined wall thickness, the catheter body member having a proximal end, a distal end, a lumen extending between the proximal and distal ends, and a distal lumen opening, the catheter body further having a truncated length to access a peripheral vein of a patient. In some implementations, the peripheral catheter further comprises a recess formed in the outer surface of the catheter body, wherein a hole is provided within the recess through the predetermined wall thickness and in communication with the lumen. As such, the recessed location of the diffusion hole is removed from directly contacting the skin or other tissues of the patient during insertion of the catheter. Accordingly, the diffusion hole is prevented from snagging the skin or tissues of the patient.

The present invention further includes methods for manufacturing an intravenous catheter for diffusing an infusant. Some methods include the steps of providing an intravenous catheter and forming a plurality of staggered holes through the wall thickness of the intravenous catheter. Some methods of the present invention further include using a laser drill to provide the various staggered holes. Still further, some methods of the present invention include extrusion and co-extrusion processes for providing the catheter body and various other features discussed in detail below.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

Embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
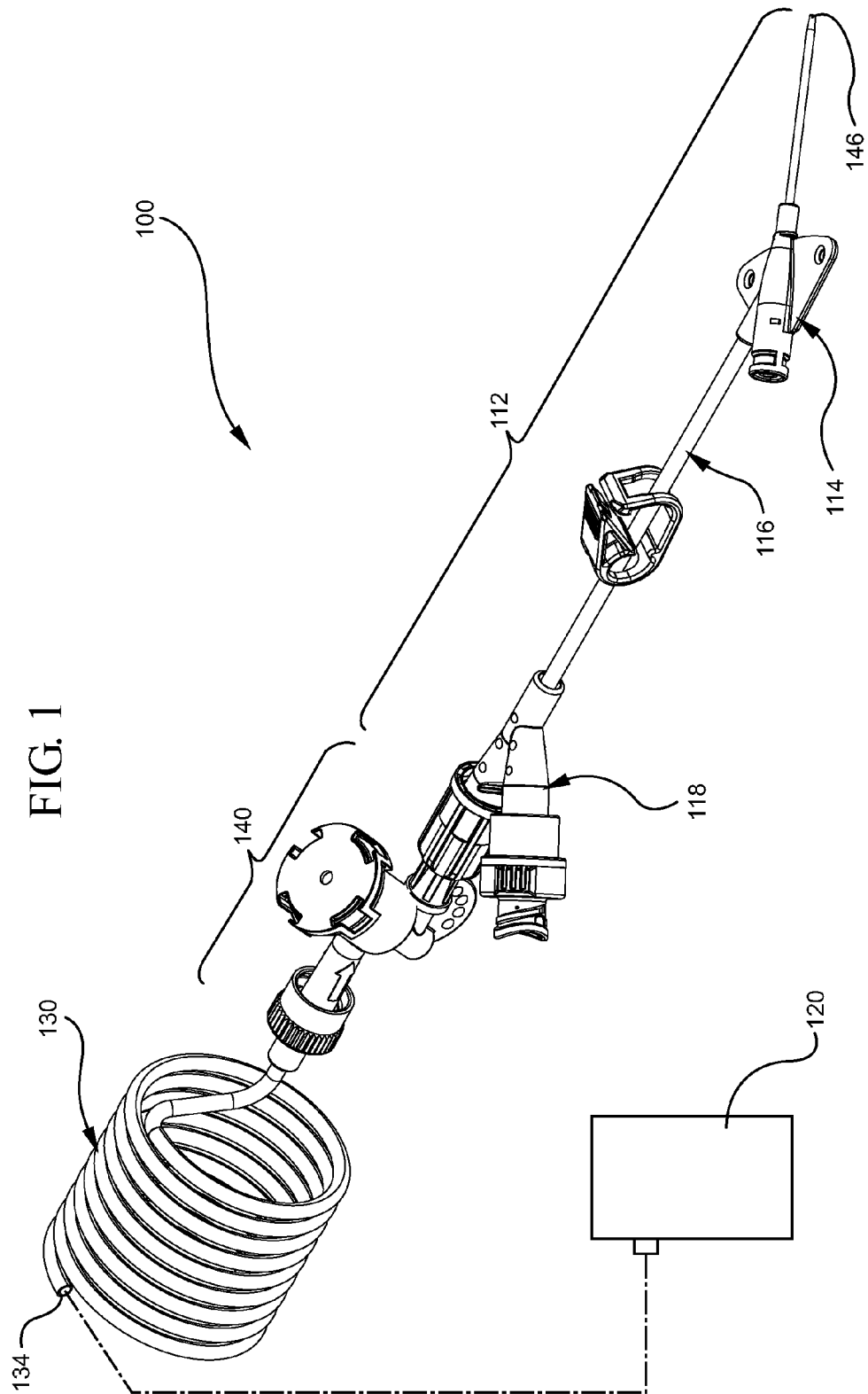
FIG. 1 is a perspective view of an infusion system in accordance with a representative embodiment of the present invention.

The systems and methods of the present invention are generally designed for use in combination with a vascular infusion system capable of rapidly delivering an infusant to the vascular system of a patient. Referring now to FIG. 1, a vascular infusion system 100 is shown, in accordance with a representative embodiment of the present invention. Infusion systems of this type are commonly configured to operate at internal pressures up to 2000 psi. Many systems operate in the range of 75 to 2000 psi, while specific devices of this type operate at 100, 200, and 300 psi. The vascular infusion system 100 comprises a vascular access device 112 coupled to an injector pump 120 via a coiled extension set 130. In some embodiments, the infusion system 100 further comprises a safety device 140 positioned between the vascular access device 112 and the injector pump 120. In some embodiments, a safety device 140 is provided to automatically occlude the fluid path of the infusion system 100, thereby preventing excessive pressure buildup in downstream infusion components.

An injector pump 120 generally comprises a fluid pumping apparatus configured to rapidly deliver an infusant, such as blood, medicaments, and CT scan contrast agents to a patient's vascular system. Desirable infusants may also include various fluids often of high viscosity as required for medical and diagnostic procedures. In some embodiments, the injector pump 120 comprises a power injector capable of delivering an infusant to a patient at flow rates from about 10 mL/hour up to about 1200 mL/minute. In some embodiments, a high infusion flow rate is desirable for medical procedures which require enhanced bolus density of an infusant in a patient's vascular system. For example, a trend in diagnostic imaging procedures is to utilize contrast media enhancement, which requires more viscous contrast media to be pushed into a patient at a higher flow rate, thereby resulting in increased image quality. Thus, in some embodiments an injector pump 120 and a vascular access device 112 are selected to compatibly achieve a desired infusion flow rate.

A coiled extension set 130 generally comprises flexible or semi-flexible polymer tubing configured to deliver an infusant from the injector pump 120 to the vascular access device 112. The extension set 130 includes a first coupler 132 for connecting the extension set 130 to a downstream device 112 or 140. The extension set 130 also includes a second coupler 134 for connecting the extension set 130 to the injector pump 120. A coiled configuration of the extension set 130 generally prevents undesirable kinking or occlusion of the set 130 during infusion procedures. However, one of skill in the art will appreciate that the extension set 130 may include any configuration capable of efficiently delivering an infusant from an injector pump 120 to the patient via a vascular access device 112. In some embodiments, the extension set 130 is coupled between a syringe and a vascular access device whereby an infusant is manually injected into a patient. In other embodiments, the infusion system comprises only a syringe and a vascular access device, in accordance with the present invention.

The vascular access device 112 generally comprises a peripheral intravenous catheter 114. A peripheral intravenous catheter 114 in accordance with the present invention generally comprises a short or truncated catheter (usually 13 mm to 52 mm) that is inserted into a small peripheral vein. Such catheters generally comprise a diameter of approximately a 14 gauge catheter or smaller. Peripheral intravenous catheters 114 are typically designed for temporary placement. The short length of the catheter 114 facilitates convenient placement of the catheter but makes them prone to premature dislodging from the vein due to movement of the patient and/or recoil forces experienced during infusion procedures. Furthermore, unlike midline or central peripheral catheters, peripheral intravenous catheters 114 in accordance with the present invention comprise a tapered catheter tip 146 to accommodate use with an introducer needle (not shown) designed to aid in insertion of the catheter 114.

An introducer needle is typically inserted through the catheter 114 such that a tip of the needle extends beyond the tapered tip 146. The tapered geometry of the tapered tip 146 conforms tightly to the outer surface of the introducer needle. Both the outer surface and the inner surface of the tip 146 are tapered towards the distal end of the catheter 114. The outer surface of the tip 146 is tapered to provide a smooth transition from the smaller profile of the introducer needle to the larger profile of the catheter outer diameter. Insertion of the introducer needle into the vein of the patient provides an opening into the vein through which the tapered tip 146 of the catheter 114 is inserted. The tapered outer surface of the tip 146 enables easy insertion of the catheter 114 into the opening. Once the peripheral intravenous catheter 114 is inserted into the vein of the patient, the introducer needle (not shown) is removed from the lumen of the catheter 114 to permit infusion via the catheter 114.

A desired infusant is typically delivered to the catheter 114 via a section of intravenous tubing 116 coupled to the catheter 114. In some embodiments, a y-adapter 118 is coupled to an end of the tubing 116 opposite the catheter 114, enabling the vascular access device 112 to be coupled to the remainder of the vascular infusion system 100. One of skill in the art will appreciate the possible variations and specific features of available vascular access devices 112, as are commonly used in the medical and research professions. For example, in some embodiments a catheter 114 in accordance with the present invention may include additional access sites, clamps, parallel intravenous lines, valves, couplers, introducer needles, coatings, and/or materials as desired to fit a specific application.

Figure 2:
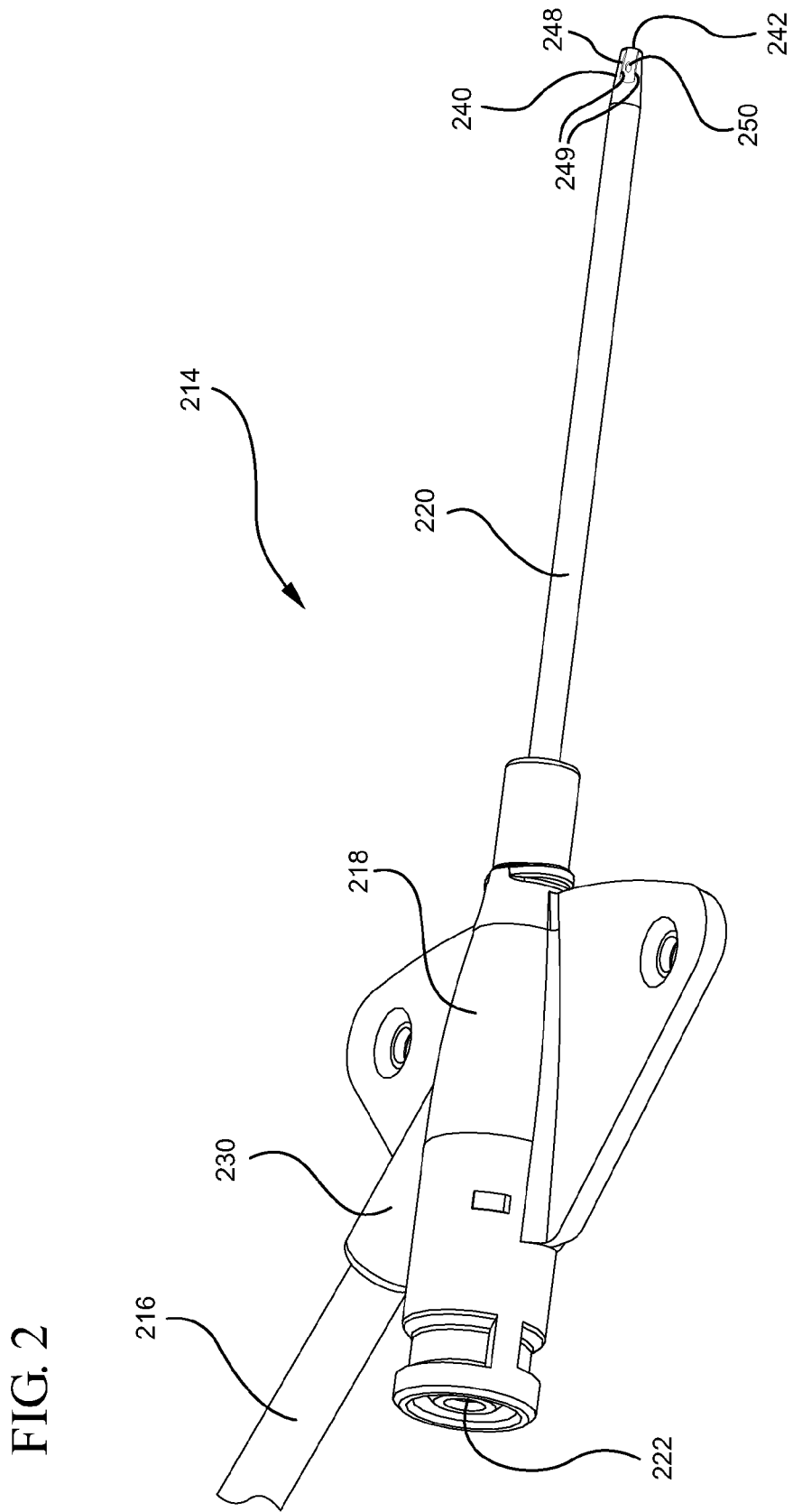
FIG. 2 is a detailed perspective view of a catheter in accordance with a representative embodiment of the present invention.

Referring now to FIG. 2, a catheter 214 is shown in accordance with a representative embodiment of the present invention. Catheter 214 generally comprises a catheter adapter 218 configured to house a tubular body member 220. Catheter adapter 218 further includes an inlet port 230 that is coupled to a section of intravenous tubing 216. The section of intravenous tubing 216 is further coupled to upstream infusion components, as shown and described in connection with FIG. 1, above.

The catheter adapter 218 facilitates delivery of an infusant within the intravenous tubing 216 to a patient via the tubular body member 220. An inner lumen of the catheter adapter 218 is in fluid communication with both an inner lumen of the intravenous tubing 216 and an inner lumen of the tubular body member 220. In some embodiments, catheter adapter 218 further comprises an access port 222. The access port 222 is generally provided to permit direct access to the inner lumen of the catheter adapter 218. In some embodiments, the access port 222 is accessed via a needle and a syringe to deliver an infusant to a patient via the tubular body member 220. In other embodiments, an introducer needle or guide wire is inserted into the access port 222 and advanced through the inner lumen of the tubular body member 220. In some embodiments, a tip portion of the introducer needle or guide wire (not shown) extends beyond a tip portion 240 of the tubular body member 220. As such, the tip portion of the introducer needle or guide wire may provide an opening into the vascular system of a patient into which the tubular body member 220 is inserted. Following placement of the tubular body member 220 into the vein of the patient, the introducer needle or guide wire is removed from the access port 222 thereby establishing fluid communication between the tubular body member 220, the catheter adapter 218 and the intravenous tubing 216.

In some embodiments, the tubular body member 220 comprises an intravenous catheter. The intravenous catheter 220 generally comprises a flexible or semi-flexible biocompatible material, as commonly used in the art. In some embodiments, the intravenous catheter 220 comprises a polymer material, such as polypropylene, polystyrene, polyvinylchloride, polytetrafluoroethylene, and the like. In other embodiments, the intravenous catheter 220 comprises a metallic material, such as surgical steel, titanium, cobalt steel, and the like.

The tubular body member 220 may comprise any length, where the length is selected based on the intended application of the catheter 214. For some applications, the tubular body member 220 is inserted into a peripheral vein of the patient. In other applications, the tubular body member 220 is inserted into a central vein of the patient. In some embodiments, the tip portion 240 of the tubular body member 220 is modified to include a recess 248 formed in the wall thickness of the tubular body member 220, as shown in FIGS. 2 and 3.

Figure 3:
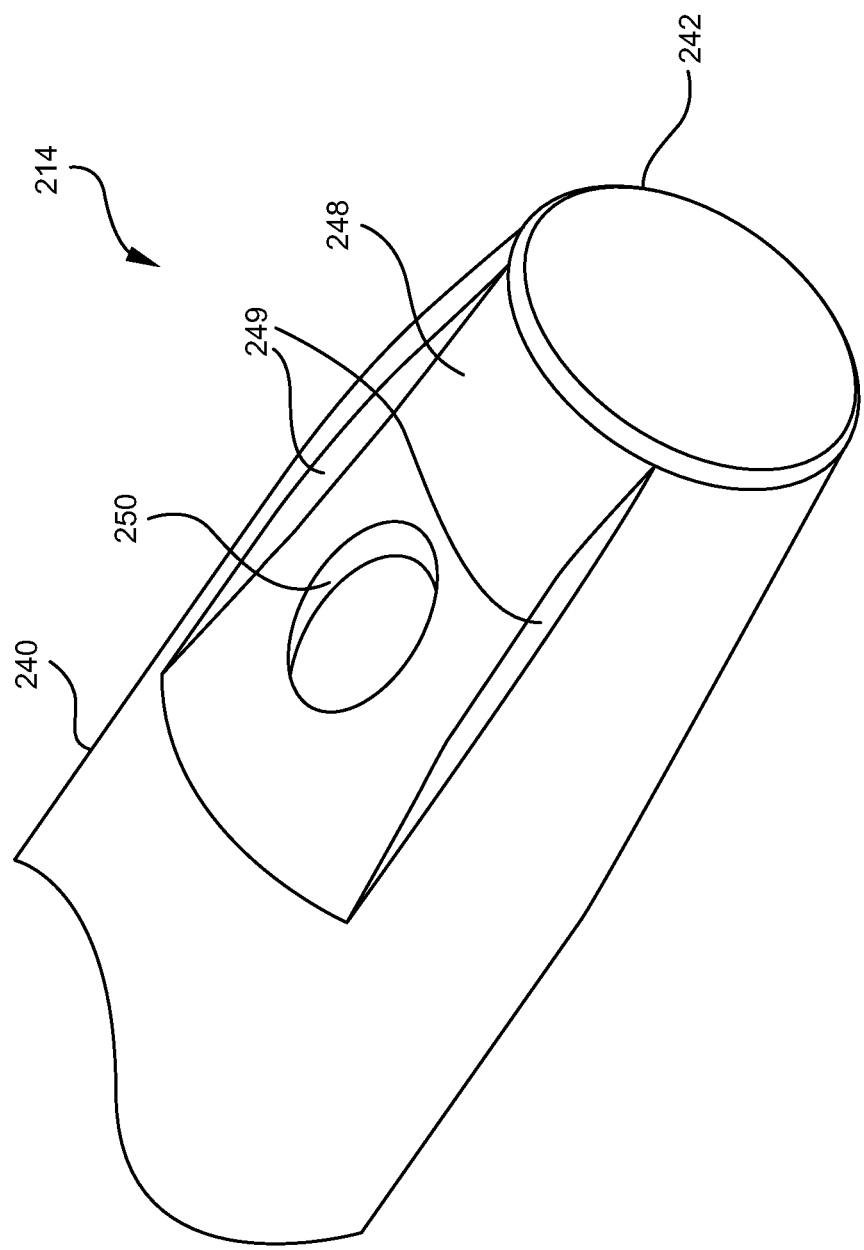
FIG. 3 is a perspective view of a catheter tip in accordance with a representative embodiment of the present invention.

With continued reference to FIGS. 2 and 3, recess 248 generally comprises a small concavity defined by adjacent sidewalls or chamfered surfaces 249. In some embodiments recess 248 further comprises a diffusion hole 250 to facilitate rapid infusion applications. Diffusion hole 250 is generally provided to divert fluid from the main channel of flow through the inner lumen of the tubular body member 220. As such, diffusion hole 250 effectually slow the jet of infusant which issues from the catheter tip 240 during rapid infusion procedures. Additionally, diffusion hole 250 increases the accumulative area of the catheter tip opening 242 to relieve the overall pressure in the vascular infusion system 100. In some embodiments, diffusion hole 250 comprises one or more side holes which meet the requirements of International Standard ISO 10555-2, section 4.4.3.

Figure 4:
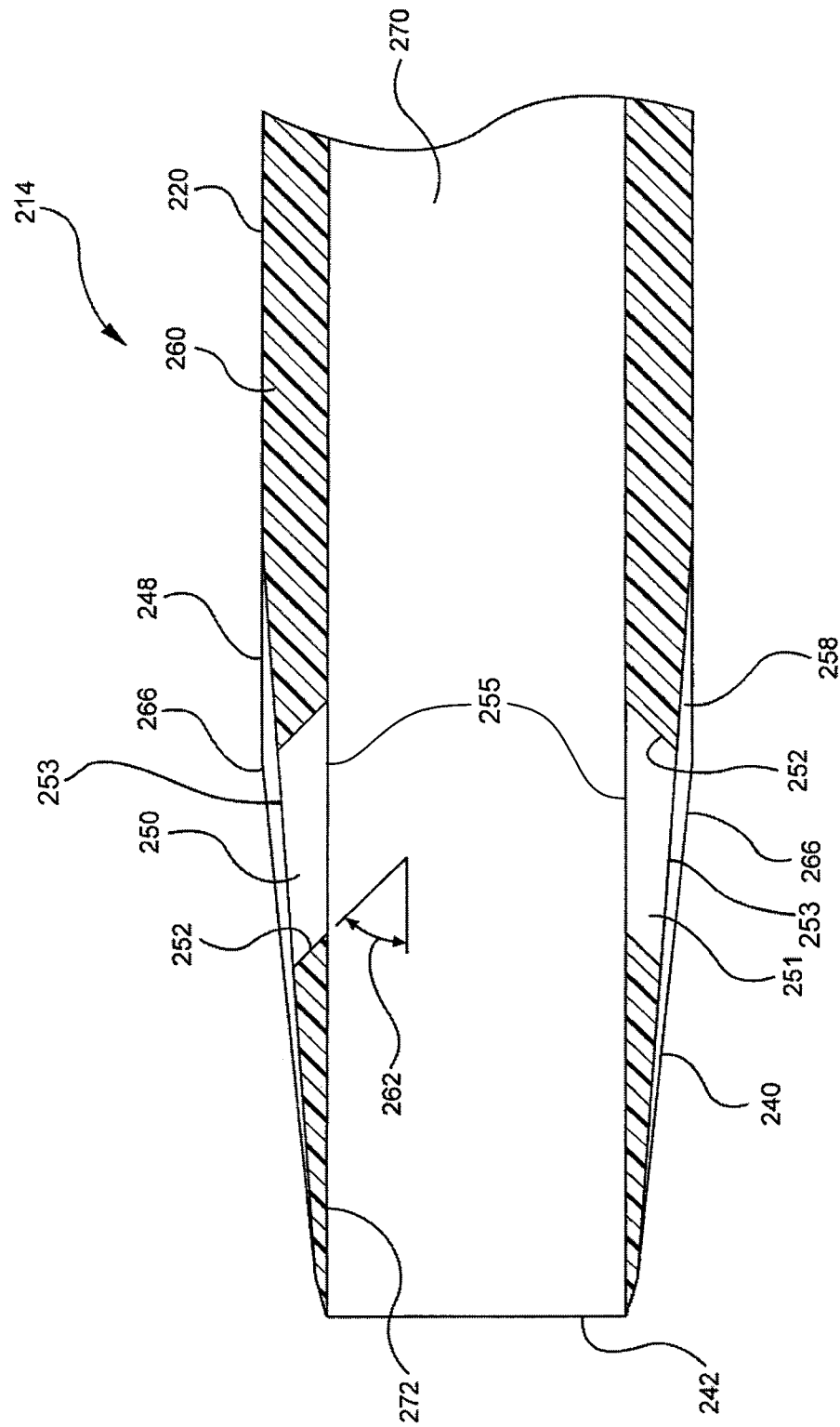
FIG. 4 is a cross-section side view of the catheter tip in accordance with a representative embodiment of the present invention.

In some embodiments, tubular body member 220 further comprises a plurality of recesses, as shown in FIG. 4. For example, in some embodiments tubular body member 220 comprises a second recess 258 positioned opposite recess 248. Second recess 258 further comprises a second diffusion hole 251 positioned opposite diffusion hole 250. In some embodiments, a plurality of recesses and diffusion holes are provided in adjacent, annular rings along the length of tubular body member 220. In other embodiments, the plurality of recess and diffusion holes are provided in a staggered pattern of adjacent, annular rings along the length of tubular body member 220. As such, an upstream recess and diffusion hole is unaligned with an adjacent, downstream recess and diffusion hole.

Recesses 248 and 258 are generally provided by manufacturing methods known in the art. For example, in some embodiments recesses 248 and 258 are provided via an extrusion process. In other embodiments, recesses 248 and 258 are provided via an etching process, such as laser etching. Further, diffusion holes 250 and 251 are generally provided by manufacturing methods known in the art. For example, in some embodiments the plurality of diffusion holes 250 and 251 are provided with a laser drill.

In some embodiments, recesses 248 and 258 are symmetrically positioned on tubular body member 220 so as to prevent catheter tip 240 from being displaced due to lateral forces causes by an infusant exiting diffusion holes 250 and 251. For example, in some embodiments a tubular body member 220 is provided having three recesses, wherein each recess comprises a diffusion hole radially spaced approximately 120° from an adjacent diffusion hole. In further example, some embodiments comprise a tubular body member 220 having greater than three recesses and greater than three diffusion holes.

Alternatively, in some embodiments tubular body member 220 is modified to include a plurality of axial ridges 266 formed on the outer surface of tubular body member 220 by extrusion or another heat forming method. Diffusion holes 250 and 251 may be placed between axial ridges 266, as shown. During catheterization (i.e.: insertion of tubular body 220 into the vascular system of a patient), axial ridges 266 lift the skin and other tissues of the patient over diffusion holes 250 and 251 thereby preventing tissue from getting snagged in the diffusion holes, as discussed below.

In some embodiments, diffusion holes 250 and 251 are formed through the catheter wall 260 such that an inner surface 252 of each hole is oriented at an angle 262 that is oblique to an inner surface 272 of the catheter lumen 270. In some embodiments, angle 262 is between about 15° to about 75°. In other embodiments, angle 262 is approximately 45°. Further, in some embodiments angle 262 is approximately 90° relative to inner surface 252.

In some embodiments, the bore angle 262 further affects the positioning of the catheter within the vein of patient. For example, when inserted into a vein the venous catheter generally extends through the skin and into the vein at approximately 30°. As such, the tip of the venous catheter commonly contacts or rests against the inner wall of the vein opposite the insertion site of the catheter. As fluid flow increases, high jet velocity from the catheter tip is exerted directly on the inner wall of the vein. However, when the tip of the venous catheter is modified to include diffusion holes, the diverted infusant that issues from the diffusion holes pushes the catheter tip away from the vein wall resulting in a centralized position of the catheter tip within the vein. Thus, the jet velocity from the tip is directed into the fluid stream of the vein rather than into the vein wall. Accordingly, in some embodiments the bore angle 262 of diffusion holes 250 and 251 is selected to achieve optimal centralized positioning of catheter tip 240 within the vasculature of the patient during infusion procedures.

Figure 5:
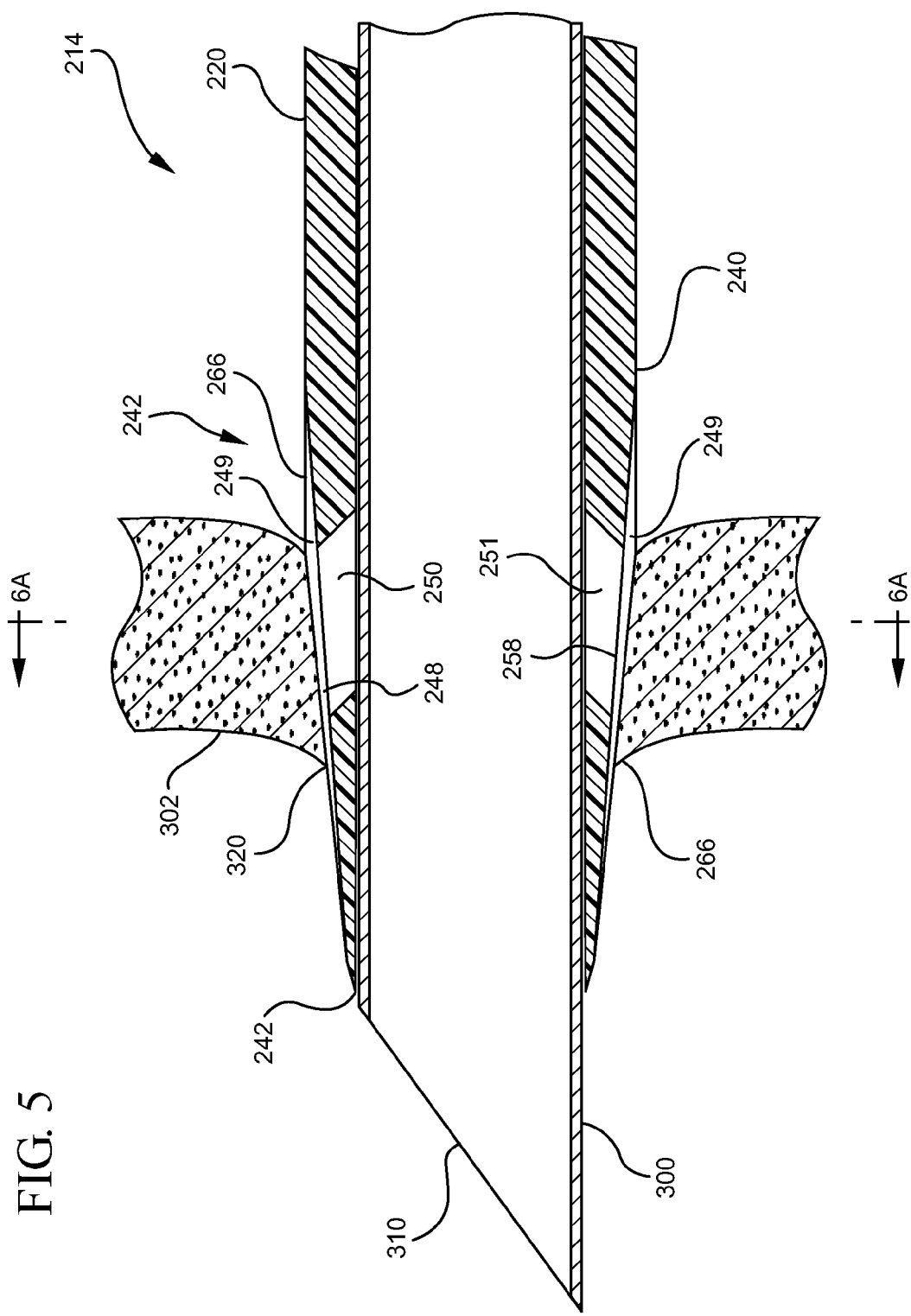
FIG. 5 is a cross-section side view of a catheter tip during catheterization in accordance with a representative embodiment of the present invention.

Referring now to FIG. 5, a distal end portion 242 of venous catheter 214 is shown, in accordance with a representative embodiment of the present invention. As previously discussed, in some embodiments an outer surface of catheter tip 240 is tapered so as to provide a gradual transition from catheter opening 242 of tip 240 to the diameter of tubular body 220. Further, in some embodiments the outer surface of catheter tip 240 is tapered so as to provide a gradual transition from the outer diameter of an introducer needle 300 to the diameter of tubular body 220, as shown.

In some embodiments, venous catheter 214 comprises an over-the-needle catheter. Thus, in some embodiments an opening 320 is provided within the skin 302 or other tissue of the patient by an introducer needle 300 housed within the catheter lumen 270. In some embodiments, a tip 310 of the introducer needle 300 is positioned external to the catheter lumen 270 so as to provide an exposed cutting surface by which to provide an opening 320 into the vasculature of the patient. Upon advancing the venous catheter into the patient, the tapered configuration of tubular body 220 permits easy passage of the catheter's tip 240 in opening 320.

As shown, axial ridges 266 lift the skin 302 or other tissues of the patient away from diffusion holes 250 and 251 during catheterization. Alternatively, recesses 248 and 258 position diffusion holes 250 and 251 away from opening 320 thereby preventing undesirable contact or snagging between the diffusion holes and opening 320. Thus, in some embodiments axial ridges 266 and/or recesses 248 and 258 increase the snag-resistance of catheter tip 240, as shown in FIG. 6A.

Figure 6A:
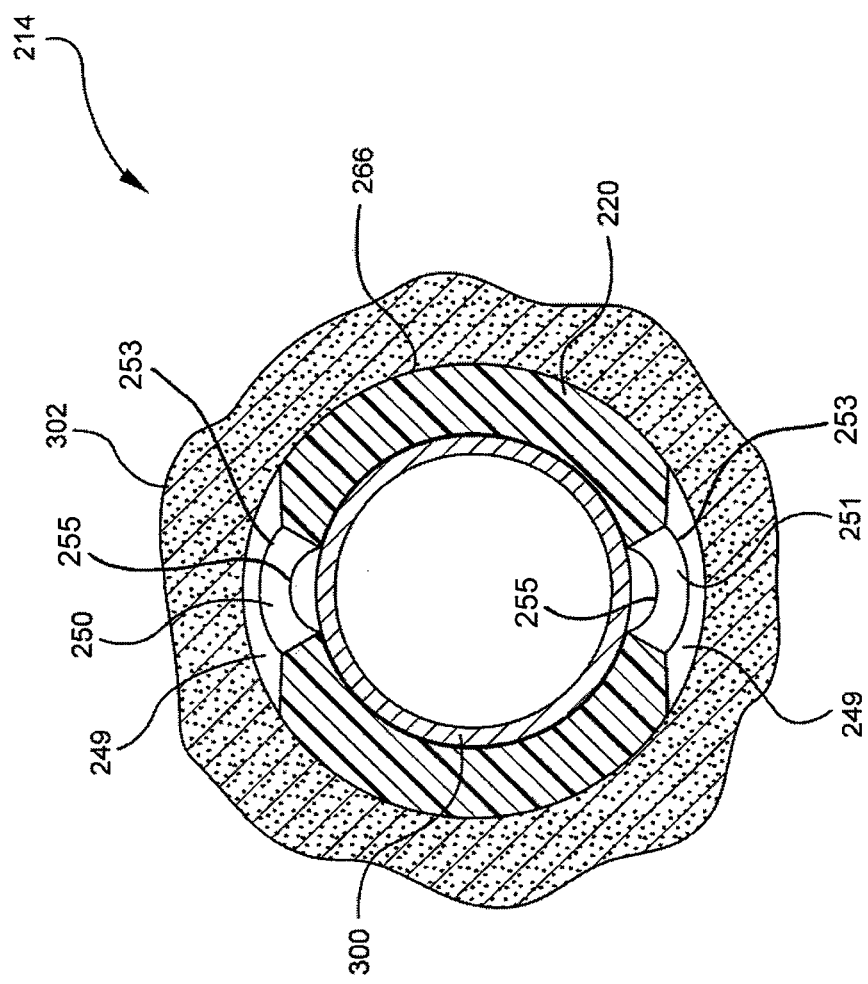
FIG. 6A is a cross-section end view of a catheter tip during catheterization in accordance with a representative embodiment of the present invention.

With continued reference to FIG. 6A, in some instances diffusion holes 250 and 251 further comprise an outer opening 253 having a perimeter defining a first surface area, and an inner opening 255 having a perimeter defining a second surface area, wherein the first surface area is greater than the second surface area. In other instances, the first surface area of outer opening 253 is less than the second surface area of inner opening 255, as shown in FIG. 4.

In some embodiments, the inclusion of diffusion holes at or near the tip of a short catheter may result in a reduction of buckling resistance for the catheter thereby making the catheter more susceptible to crushing during catheterization. Accordingly, in some embodiments axial ridges 266 further increase the bending and buckling stiffness of catheter tip 240, thereby minimizing the risks of catheter tip crushing or buckling during insertion. One having ordinary skill in the art will therefore appreciate and recognize that the stiffening effect of axial ridges 266 may be accomplished by any number of structural modifications wherein the thickness and/or rigidity of the catheter wall 260 between diffusion holes 250 and 251 is increased to withstand compression and/or sheer forces during insertion.

Figure 6B:
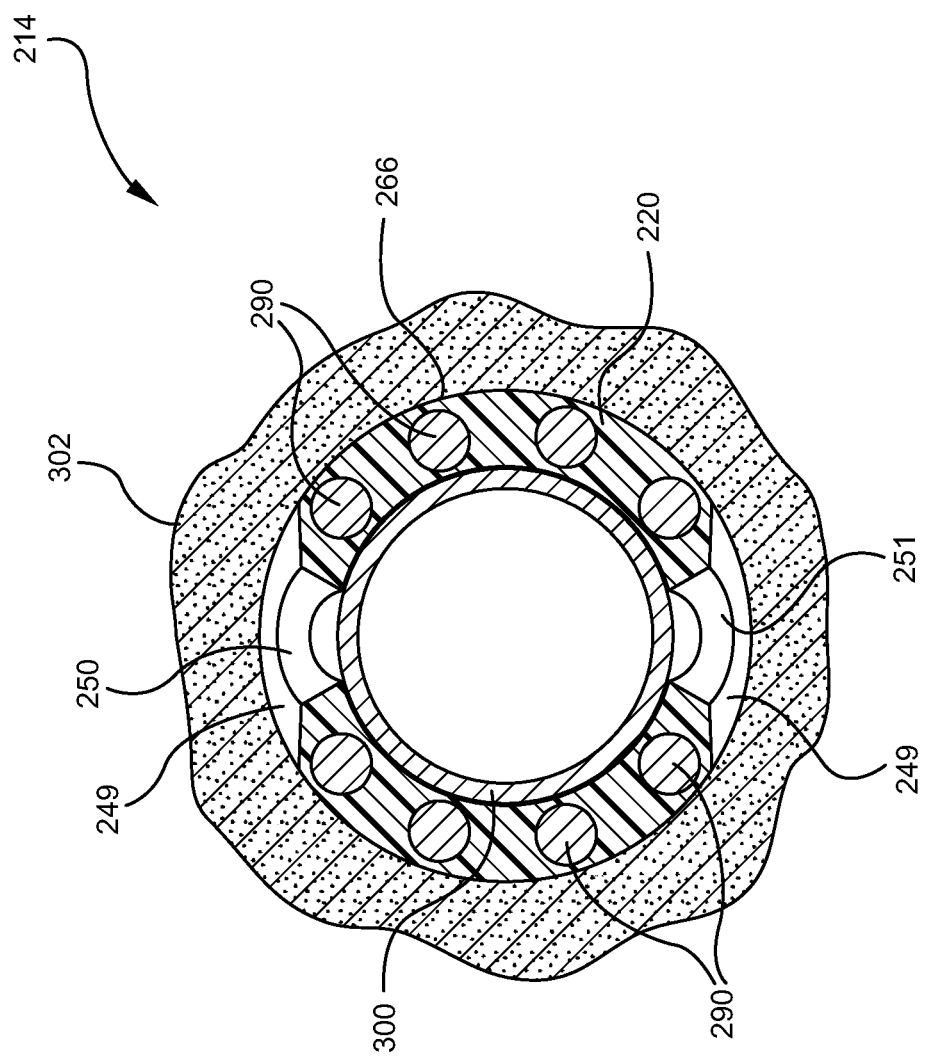
FIG. 6B is a cross-section end view of a catheter tip during catheterization, the catheter tip incorporating a stiffening material in accordance with a representative embodiment of the present invention.

For example, in some embodiments the rigidity of the catheter wall 260 positioned between diffusion holes 250 and 251 is increased by the addition of a stiffening material 290, as shown in FIG. 6B. In some embodiments, stiffening material comprises a rigid or semi-rigid radiopaque material, such as a wire or an extruded filler material which may include a chemical salt of bismuth or barium, or an element such as platinum or tungsten. In some embodiments stiffening material 290 comprises barium sulfate. In other embodiments, stiffening material 290 comprises a polymer material having an increased density as compared to the remaining polymer material of the venous catheter 214. In some embodiments, venous catheter 214 and stiffening material 290 are coextruded, wherein stiffening material 290 is embedded within the wall thickness of the tubular body member 220. In other embodiments, stiffening material 290 is applied directly to the external surface of tubular body member 220, thereby forming axial ridges 266.

Figure 7:
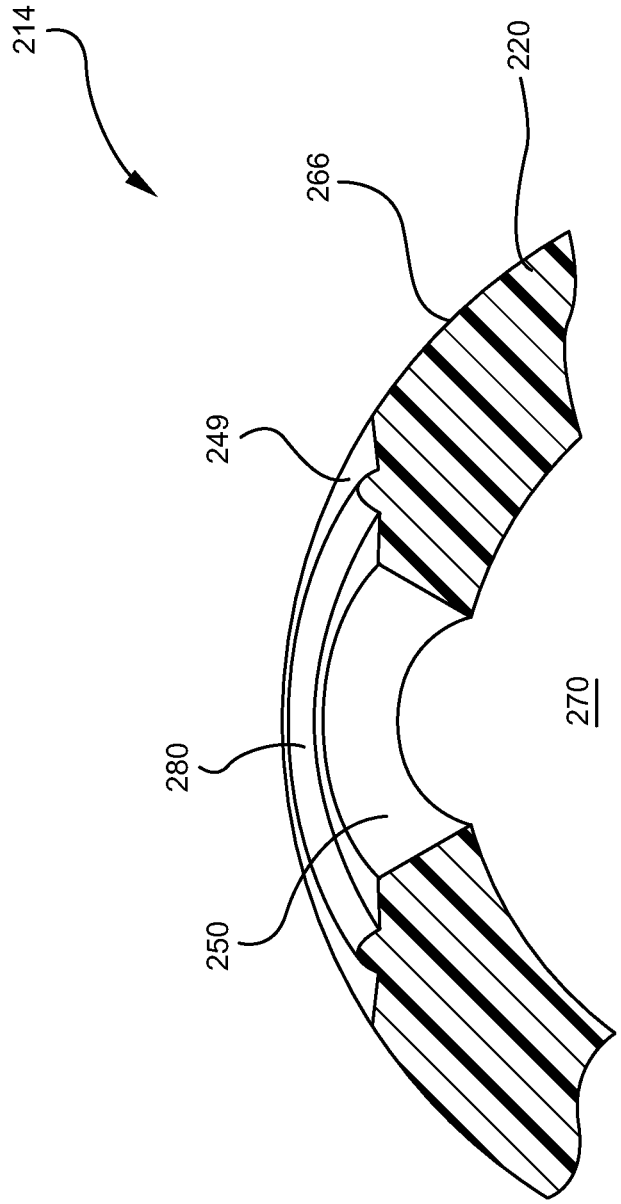
FIG. 7 is a detailed cross-section end view of a catheter tip having a flow breaking feature in accordance with a representative embodiment of the present invention.

Referring now to FIG. 7, in some embodiments sidewalls 249 further comprise a flow breaking feature 280. A "flow breaking feature" refers to a feature of the diffusion hole 250 and/or a physical feature adjacent to the diffusion hole 250 that substantially breaks up, thins, or slows a jet of infusant exiting the diffusion hole 250 so that the jet will lose speed more quickly within the vein.

FIGS. 2-7 generally depict circular diffusion holes. However, in some embodiments one or more diffusion holes may be non-circular. For example, in some embodiments flow breaking feature 280 may include a flow disrupter, elongated diffusion hole geometries, and diffusion hole orientations such that the axis of flow of two or more diffusion holes collide. In some embodiments, flow breaking feature 280 is a flow disrupter comprising an inward projection that contacts the jet of infusant exiting diffusion hole 250. In other embodiments, flow breaking feature 280 is a flow disrupter including a pointed extension. Further, in some embodiments feature 280 comprises a plurality of inward projections. An "inward projection" refers to a portion of a diffusion hole's periphery which projects toward the inner portion of the diffusion hole.

In some embodiments, a single diffusion hole includes more than one flow breaking features. Examples of flow breaking features are described herein, including at least inward projections, wedged extensions, an elongated diffusion hole geometry, and diffusion hole axis orientations that result in collisions with other fluid jets. For example, in some embodiments, a diffusion hole includes an inward projection and has an axis orientation that collides with that of another hole. In addition, in some embodiments the diffusion hole further includes a wedged extension. In other embodiments, other combinations of flow breaking features are combined to provide a less harmful, more effective catheter diffusion hole and diffusion hole array configuration.

From the foregoing, it will be seen that one or more flow breaking features can be included on one or more catheter diffusion holes on a catheter tip. The flow breaking features can substantially break up, thin, or slow a jet of fluid exiting a diffusion hole so that the jet will lose speed more quickly within the vein and cause less damage to vessel walls. In particular, flow breaking features are particularly advantageous when used in rapid infusion therapy that uses highly infusant velocities to rapidly introduce a bolus of fluid into a patient through the catheter tip. During these procedures, one or more flow breaking features of a diffusion hole can increase infusion patient comfort, decrease patient pain, allow for greater infusion velocities, and prevent vessel damage.

Figure 8:
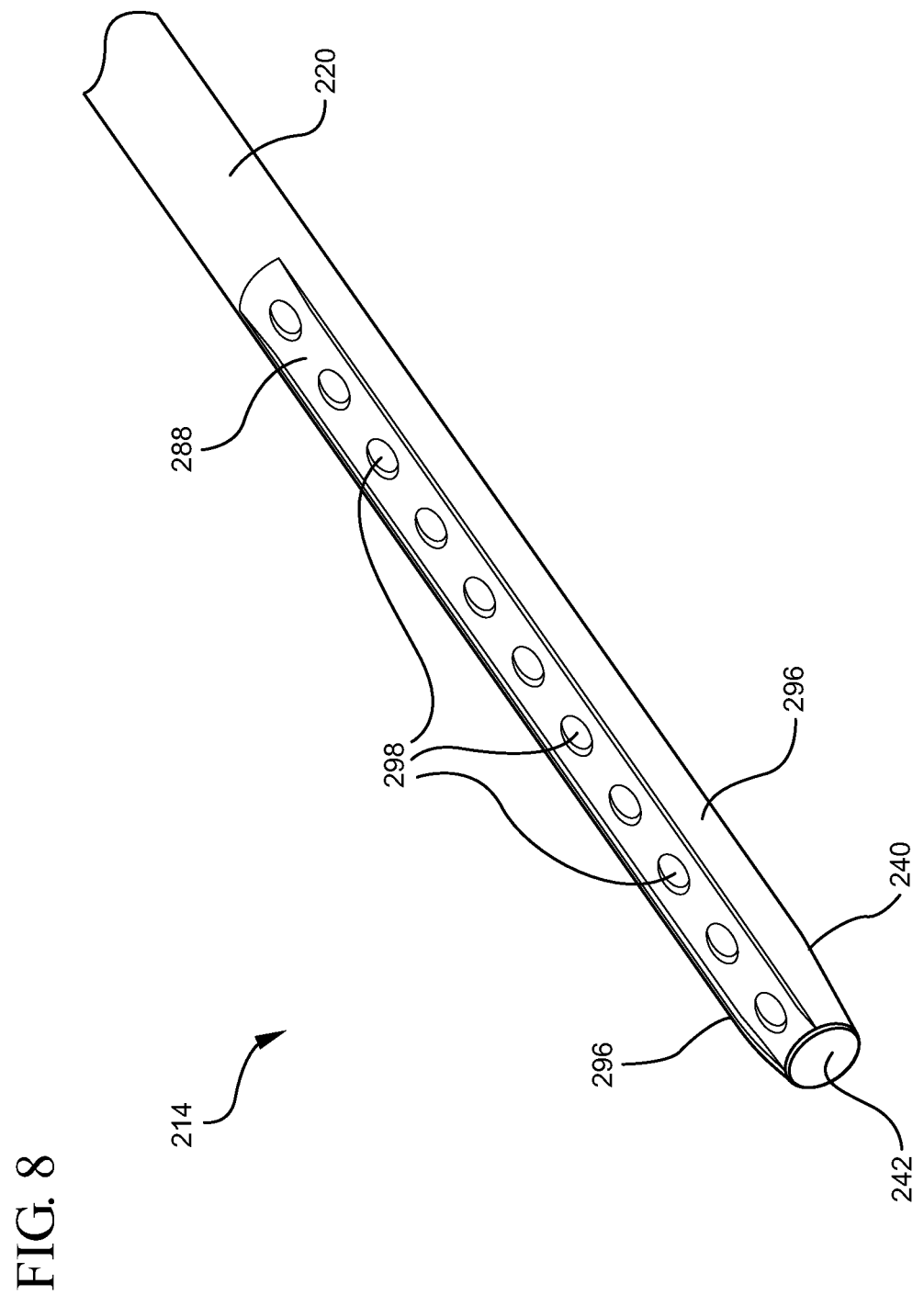
FIG. 8 is a perspective view of a catheter tip in accordance with a representative embodiment of the present invention.

Referring now to FIG. 8, in some embodiments recess 288 and axial ridges 296 are extended along the length of tubular body 220, thereby accommodating a plurality of recessed diffusion holes 298. Accordingly, the sum of the exiting infusant jets from recessed diffusion holes 298 will produce a fluid infusion with less impact energy and which poses a lesser risk to the patient's vessel walls. In some embodiments, recess 288 comprises a non-linear recess thereby providing a non-linear alignment of recessed diffusion holes 298. For example, in some embodiments recess 288 comprises a helical recess, wherein recess 288 circumscribes the outer surface of tubular member 220 in a helical fashion. In other embodiments, recess 288 comprises a plurality of longitudinal recesses, wherein a portion of each longitudinal recess is interested with a ridge thereby dividing each longitudinal recess into two or more sections.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A peripheral catheter, comprising:
    a catheter body having a central axis, an outer surface of the catheter body being coaxial with and radially spaced from the central axis at a first distance, the catheter body also including a single centrally located lumen coaxial to the central axis, the single centrally located lumen having an annular inner surface that is coaxial with and radially spaced from the central axis at a second distance, the single centrally located lumen extending between a proximal end and a distal end of the catheter body and comprising a distal lumen opening, the single centrally located lumen providing a fluid path through which power injections of fluid are transmitted from the single centrally located lumen and into a vasculature of a patient;
    a recess formed in the outer surface of the catheter body, the recess comprising opposing sidewalls that radially extend inwardly from the outer surface to a recess surface that extends between the opposing sidewalls, the recess surface being located at a third distance from the central axis, wherein the third distance is between the first distance and the second distance; and
    a hole formed through the recess surface and into the single centrally located lumen such that power injected fluids exit the single centrally located lumen via the distal lumen opening and the hole positioned in the recess, the hole comprising a sidewall having an outer edge, the outer edge located at the third distance and an inner edge located at the second distance, the hole also being positioned completely within the recess such that there is a portion of the recess surface between the sidewall of the hole and each sidewall of the recess.

2. The peripheral catheter of claim 1, wherein the hole comprises a plurality of holes through which the power injected fluids exit the single centrally located lumen.

3. The peripheral catheter of claim 1, further comprising a plurality of recesses, wherein each of the recesses comprises at least one hole through which the power injected fluids exit the single centrally located lumen.

4. The peripheral catheter of claim 1, wherein the catheter body includes a tapered distal end, the recess being formed in the tapered distal end such that the first, second, and third distances are tapered.

5. The peripheral catheter of claim 4, further comprising a flow breaking feature positioned on a chamfered surface.

6. The peripheral catheter of claim 5, wherein the flow breaking feature includes a flow disrupter.

7. The peripheral catheter of claim 6, wherein the flow disrupter is an inward projection.

8. The peripheral catheter of claim 1, wherein a bore angle of the hole is oblique to an inner wall surface of the single centrally located lumen.

9. A method for manufacturing a snag-resistant, vented peripheral catheter, the method comprising:
providing a catheter body having a central axis, an outer surface of the catheter body being coaxial with and radially spaced from the central axis at a first distance, the catheter body also including a single centrally located lumen coaxial to the central axis, the single centrally located lumen having an annular inner surface that is coaxial with and radially spaced from the central axis at a second distance, the single centrally located lumen extending between a proximal end, and a distal end of the catheter body and comprising a distal lumen opening, the single centrally located lumen providing a fluid path through which power injections of fluid are transmitted from the single centrally located lumen and into a vasculature of a patient;
providing a recess in the outer surface of the catheter body, the recess comprising opposing sidewalls that radially extend inwardly from the outer surface to a recess surface that extends between the opposing sidewalls, the recess surface being located at a third distance from the central axis, wherein the third distance is between the first distance and the second distance; and
providing a hole formed through the recess surface and into the single centrally located lumen such that power injected fluids exit the single centrally located lumen via the distal lumen opening and the hole positioned in the recess, the hole comprising a sidewall having an outer edge located at the third distance and an inner edge located at the second distance, the hole also being positioned completely within the recess such that there is a portion of the recess surface between the sidewall of the hole and each sidewall of the recess.

10. The method of claim 9, further comprising the step of providing a plurality of holes in the recess through which the power injected fluids exit the single centrally located lumen.

11. The method of claim 9, further comprising the step of providing a plurality of recesses, wherein each of the recesses comprises at least one hole through which the power injected fluids exit the single centrally located lumen.

12. The method of claim 9, further comprising the step of interposing a flow breaking feature between the hole and the outer surface of the catheter body.

13. The method of claim 12, wherein the flow breaking feature comprises a portion of a chamfered surface interposed between the hole and the outer surface of the catheter body.

14. The method of claim 12, wherein the flow breaking feature includes a flow disrupter.

15. The method of claim 9, wherein a bore angle of the hole is oblique to an inner wall the annular inner surface of the single centrally located lumen.

16. A vascular access device comprising:
a catheter adapter;
a catheter extending from a distal end of the catheter adapter, the catheter having a central axis, an outer surface of the catheter being coaxial with and radially spaced from the central axis at a first distance, the catheter also including a single centrally located lumen coaxial to the central axis, the single centrally located lumen having an annular inner surface that is coaxial with and radially spaced from the central axis at a second distance, the single centrally located lumen extending between a proximal end and a distal end of the catheter and comprising a distal lumen opening, the single centrally located lumen providing a fluid path through which power injections of fluid are transmitted from the single centrally located lumen and into a vasculature of a patient,
the catheter including a recess formed in the outer surface, the recess comprising opposing sidewalls that radially extend inwardly from the outer surface to a recess surface that extends between the opposing sidewalls, the recess surface being located at a third distance from the central axis, wherein the third distance is between the first distance and the second distance,
the catheter further including a hole formed through the recess surface and into the single centrally located lumen such that power injected fluids exit the single centrally located lumen via the distal lumen opening and the hole positioned in the recess, the hole comprising a sidewall having an outer edge, the outer edge located at the third distance and an inner edge located at the second distance, the hole also being positioned completely within the recess such that there is a portion of the recess surface between the sidewall of the hole and each sidewall of the recess;
an introducer needle that is contained within the single centrally located lumen and extends distally from the distal lumen opening of the catheter.

17. The vascular access device of claim 16, further comprising a flow breaking feature positioned on one or both of the sidewalls.

18. The vascular access device of claim 16, wherein the catheter further comprises a stiffening material embedded within a wall thickness of the catheter.

19. The vascular access device of claim 18, wherein the stiffening material comprises a plurality of strips of the stiffening material that are spaced within and extend along a length of a tapered tip.

20. The vascular access device of claim 16, wherein the catheter includes a tapered distal end, the recess being formed in the tapered distal end such that the first, second, and third distances are tapered.

* * * * *